United States Patent
Szuba

(10) Patent No.: US 7,035,432 B2
(45) Date of Patent: Apr. 25, 2006

(54) METHOD OF MONITORING SLEEPING INFANT

(75) Inventor: Joseph Szuba, Dearborn, MI (US)

(73) Assignee: RonJo Company, Orion, MI (US)

( * ) Notice: Subject to any disclaimer, the term of this patent is extended or adjusted under 35 U.S.C. 154(b) by 0 days.

(21) Appl. No.: 10/896,724

(22) Filed: Jul. 22, 2004

(65) Prior Publication Data

US 2005/0053262 A1    Mar. 10, 2005

Related U.S. Application Data

(60) Provisional application No. 60/489,199, filed on Jul. 22, 2003.

(51) Int. Cl.
| | |
|---|---|
| G06K 9/00 | (2006.01) |
| G06K 9/68 | (2006.01) |
| A61B 5/05 | (2006.01) |
| A61B 5/103 | (2006.01) |
| A61B 6/00 | (2006.01) |

(52) U.S. Cl. .................. 382/103; 382/107; 382/128; 382/218; 600/407; 600/473; 600/476; 600/534; 600/595

(58) Field of Classification Search ............... 382/103, 382/107, 115, 128, 154, 209, 217, 218, 219, 382/278; 600/407, 473, 474, 475, 476, 477, 600/529, 534, 595
See application file for complete search history.

(56) References Cited

U.S. PATENT DOCUMENTS

| | | | |
|---|---|---|---|
| 4,350,166 A | 9/1982 | Mobarry | |
| 5,517,251 A * | 5/1996 | Rector et al. ............... | 348/476 |
| 5,653,462 A | 8/1997 | Breed et al. | |
| 5,694,320 A | 12/1997 | Breed | |
| 5,748,473 A | 5/1998 | Breed et al. | |
| 5,822,707 A | 10/1998 | Breed et al. | |
| 5,829,782 A | 11/1998 | Breed et al. | |
| 5,835,613 A | 11/1998 | Breed et al. | |
| 5,845,000 A | 12/1998 | Breed et al. | |
| 5,848,802 A | 12/1998 | Breed et al. | |
| 5,901,978 A | 5/1999 | Breed et al. | |
| 5,914,660 A * | 6/1999 | Mesibov et al. ......... | 340/573.7 |
| 5,943,295 A | 8/1999 | Varga et al. | |
| 6,039,139 A | 3/2000 | Breed et al. | |
| 6,062,216 A * | 5/2000 | Corn ..................... | 128/204.23 |
| 6,078,854 A | 6/2000 | Breed et al. | |
| 6,081,757 A | 6/2000 | Breed et al. | |
| 6,088,640 A | 7/2000 | Breed | |
| 6,116,639 A | 9/2000 | Breed et al. | |
| 6,134,492 A | 10/2000 | Breed et al. | |
| 6,141,432 A | 10/2000 | Breed et al. | |
| 6,168,198 B1 | 1/2001 | Breed et al. | |
| 6,186,537 B1 | 2/2001 | Breed et al. | |
| 6,234,519 B1 | 5/2001 | Breed | |
| 6,234,520 B1 | 5/2001 | Breed et al. | |

(Continued)

*Primary Examiner*—Jingge Wu
*Assistant Examiner*—Anthony Mackowey
(74) *Attorney, Agent, or Firm*—Howard & Howard

(57) ABSTRACT

A method of detecting high risk movements of an infant relating to Sudden Infant Death Syndrome includes generating a reference image of an infant by signaling a controller a location of a first plurality of pixels. The first plurality of pixels are stored in a controller generating a reference image. A second electronic image of the infant is generating a second plurality of pixels that are signaled to the controller. The controller compares the second electronic image to the first electronic image by determining a correlation between the first plurality of pixels to the second plurality of pixels for determining if the infant has made a high risk movement.

11 Claims, 2 Drawing Sheets

U.S. PATENT DOCUMENTS

| | | |
|---|---|---|
| 6,242,701 B1 | 6/2001 | Breed et al. |
| 6,253,134 B1 | 6/2001 | Breed et al. |
| RE37,260 E | 7/2001 | Varga et al. |
| 6,270,116 B1 | 8/2001 | Breed et al. |
| 6,279,946 B1 | 8/2001 | Johnson et al. |
| 6,283,503 B1 | 9/2001 | Breed et al. |
| 6,324,453 B1 | 11/2001 | Breed et al. |
| 6,325,414 B1 | 12/2001 | Breed et al. |
| 6,330,501 B1 | 12/2001 | Breed et al. |
| 6,331,014 B1 | 12/2001 | Breed |
| 6,352,517 B1* | 3/2002 | Flock et al. ................ 600/595 |
| 6,373,392 B1* | 4/2002 | Au ......................... 340/573.1 |
| 6,393,133 B1 | 5/2002 | Breed et al. |
| 6,397,136 B1 | 5/2002 | Breed et al. |
| 6,412,813 B1 | 7/2002 | Breed et al. |
| 6,422,595 B1 | 7/2002 | Breed et al. |
| 6,442,465 B1 | 8/2002 | Breed et al. |
| 6,442,504 B1 | 8/2002 | Breed et al. |
| 6,445,988 B1 | 9/2002 | Breed et al. |
| 6,452,870 B1 | 9/2002 | Breed et al. |
| 6,492,634 B1 | 12/2002 | Marchitto et al. |
| 6,553,296 B1* | 4/2003 | Breed et al. .................. 701/45 |
| 6,679,830 B1* | 1/2004 | Kolarovic et al. ............ 600/22 |
| 2001/0044588 A1* | 11/2001 | Mault ......................... 600/549 |
| 2002/0013538 A1* | 1/2002 | Teller ......................... 600/549 |
| 2002/0173696 A1 | 11/2002 | Kolarovic et al. |
| 2003/0190076 A1* | 10/2003 | DeLean ..................... 382/209 |
| 2004/0005088 A1* | 1/2004 | Jeung et al. ................ 382/128 |
| 2004/0210155 A1* | 10/2004 | Takemura et al. .......... 600/534 |

\* cited by examiner

METHOD OF MONITORING SLEEPING INFANT

RELATED APPLICATIONS

This application claims priority to U.S. Provisional Patent Application No. 60/489,199 filed on Jul. 22, 2003.

BACKGROUND OF THE INVENTION

Sudden infant death syndrome (SIDS) is a sudden and unexpected death of an apparently healthy infant whose death remains unexplained after further medical investigation. SIDS is not acknowledged as a disease, nor has it been diagnosed for a living baby. However, many SIDS deaths have been documented where an infant has been sleeping face down. A face down infant is considered by many experts in the field of infant mortality to be a high risk position for a SIDS attributed death because a face down position may lead to periods of apnea (stoppage of breathing). While infants may be resuscitated during a period of apnea, most SIDS events occur at night when the infant's caregiver is sleeping.

Attempts have been made to identify a SIDS event and provide a technological solution to early detection. Once such example, U.S. Pat. No. 4,350,166, APNEA DETECTOR, attempts to identify potential SIDS risks by the detection of long wave infrared radiation typical of carbon dioxide emitted from a breathing infant. However, this type of detector merely identifies that an infant has stopped breathing, which is too late to prevent the SIDS event from occurring. Furthermore, infant body heat can skew the detection of infrared radiation. Another such example is U.S. Pat. No. 6,492,634, OPTICAL MONITOR FOR SUDDEN INFANT DEATH SYNDROME, where a monitor tracks the movement of a laser beam or light emitting diode projected onto an infant. This device again merely tracks the breathing patterns of the infant and will only initiate an alarm if the infant has stopped breathing as indicated by the movement or lack of movement of the laser beam. Therefore, it would be desirable to provide a SIDS detection device capable of detecting high risk movement of an infant prior to any disruption in the infant's breathing pattern.

SUMMARY OF THE INVENTION

A method of detecting high risk movements of an infant relating to sudden death syndrome is disclosed. A reference image of an infant is signaled to a controller a location of a first plurality of pixels. The location of the plurality of pixels is stored in the controller generating for a reference image. A second electronic image of the infant is signaled to the controller a location of a second plurality of pixels. The second electronic image is compared to the first electronic image by determining the correlation between the first plurality of pixels to the second plurality of pixels for identifying high risk movements of the infant prior to an apnea event occurring.

The present inventive method of detecting high risk movements of an infant provides the ability to generate and transmit a distress signal prior to adverse breathing patterns developed in the infant. Unlike prior art detection systems, which identify problems with the infant based upon breathing irregularities, a caregiver now has the ability to interact with an infant before any breathing irregularities put the infant at risk. As previously stated, infants are believed to be at risk when sleeping on their front side. The inventive concept provides the ability to detect if an infant has rolled completely over even onto the infant's side while sleeping. In the event an infant rolls over or onto his/her side, a distress signal is generated and transmitted notifying the caregiver to take action prior to a sleep apnea event occurring.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE PREFERRED EMBODIMENT

Figure 1:
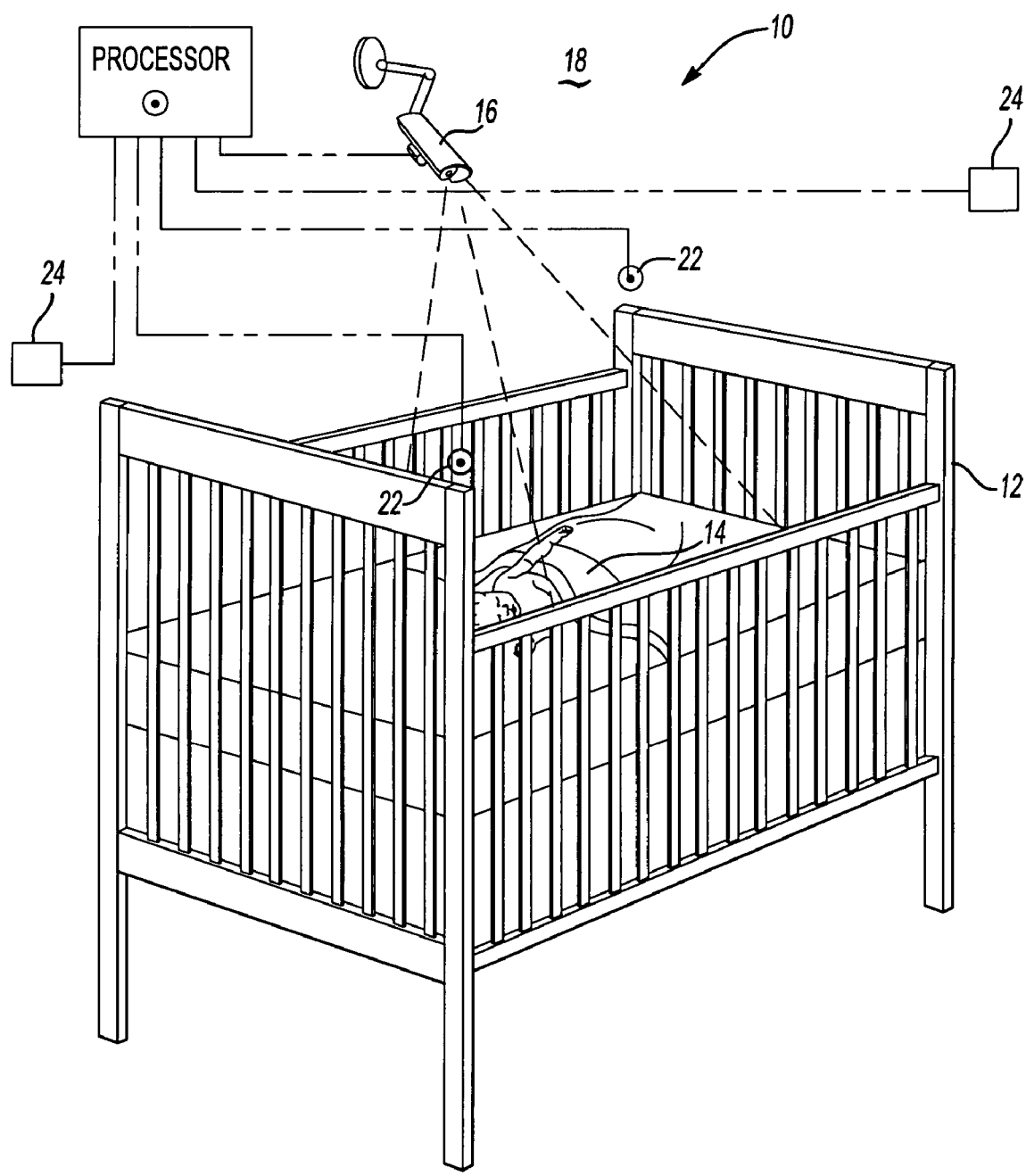
FIG. 1 shows a schematic view of a sleeping infant associated with the inventive sudden infant death syndrome detection system.

Referring to FIG. 1, a preferred embodiment of the present assembly is generally shown at 10. The assembly 10 interacts with a sleeping surface, or a crib 12, upon which an infant 14 sleeps.

A vision system or a camera 16 is placed above the infant 14 and provided with a view of, preferably, the entire infant 14. The camera 16 is preferably mounted to a wall 18, but may optionally be mounted to the crib 12 if necessary. More than one camera 16 is alternatively used to further enhance the image of the infant that is generated. As will be discussed further below, the camera 16 generates sequential images of the infant and transmits those images to a processor 20. The camera 16 is preferably hard wired to the processor 20. However, in an alternate embodiment, the camera includes an RF or equivalent transmitter and signals a remote processor (not shown) with the image of the infant 14 being generated.

Technological advances and cameras 16 have produced high resolution images capable of generating a significant number of pixels from a received image. By transmitting the image to a processor, the camera 16 enables the processor 20 to record and detect through computer algorithms minor changes in sequential images transmitted by the camera 16.

The cameras 16 is capable of generating the high resolution images that provide a high number of pixels. The camera 16 may include charge coupled cameras, high dynamic range cameras, active pixel cameras, and complementary metal oxides semi-conductor cameras and their equivalents. Each of these cameras provide the high resolution necessary to generate the plurality of pixels required for the processor 20 to measure variations in pixels between sequentially generated images. It may be necessary to provide an infrared transmitter 22 to enhance the image of the infant 14 generated by the camera 16. The infrared transmitter 22 is particularly relevant when a satisfactory amount of light is not available such as, for example, during night time. Alternatively, a camera 16 capable of detecting electromagnetic radiation also produces sufficient resolution.

The processor 20 is electronically connected to a remote signaling device 24 for when a high risk movement of the infant is determined by the processor 20 as will be explained further below. The signaling device 24 is alternatively hard wired to the processor 20 or receives a signal from the processor 20 through an RF or equivalent transmission. Preferably, a plurality of signaling devices 24 are spaced around a residence so that the infant's 14 caregiver is always within range of the signaling device 24. The signaling device 24 is alternatively an optical or sound transmitting device capable of notifying the infant's 14 caregiver of a high risk movement of the infant as detected by the processor 20 as desired.

Initially, a reference image is first generated that provides a base point for the processor 20 to begin its analysis of the infant's 14 movement. Various techniques are available to generate a reference image 26 that provides the necessary pixels required to conduct a computer algorithm required to analyze the movements of the infant 14.

A first alternative to generating the reference image 26 makes use of a doll or test dummy having the size and characteristics of an infant at the age where SIDS is known to be a risk. The camera 16 takes an image of the doll's face, and preferably body, when a doll is positioned as though sleeping on its back. Various features are identifiable by the processor 20 through the high resolution of pixels generated by the camera 16, such as, for example, eyes, nose, mouth, and chest of the infant.

An alternative to using a doll or dummy to generate a reference image 26 is to use the infant 14 as intended to be monitored by the assembly 10. In this case, additional reference images can be generated as the infant 14 grows providing an even more accurate analysis of the infant's sleeping pattern and potential for high risk movements.

An alternative reference image to the infant's 14 front is to generate a reference image of the infant's 14 side by detecting features, such as, the infant's 14 profile, ears, and shoulder. In this case, the infant 14 has already made a movement toward sleeping on his/her stomach which is regarded as the highest risk sleeping position related to SIDS. In any event, the reference image is stored in the processor 20 thereby generating a plurality of pixels necessary for the analysis and detection of the infant's 14 high risk movements.

Figure 2:
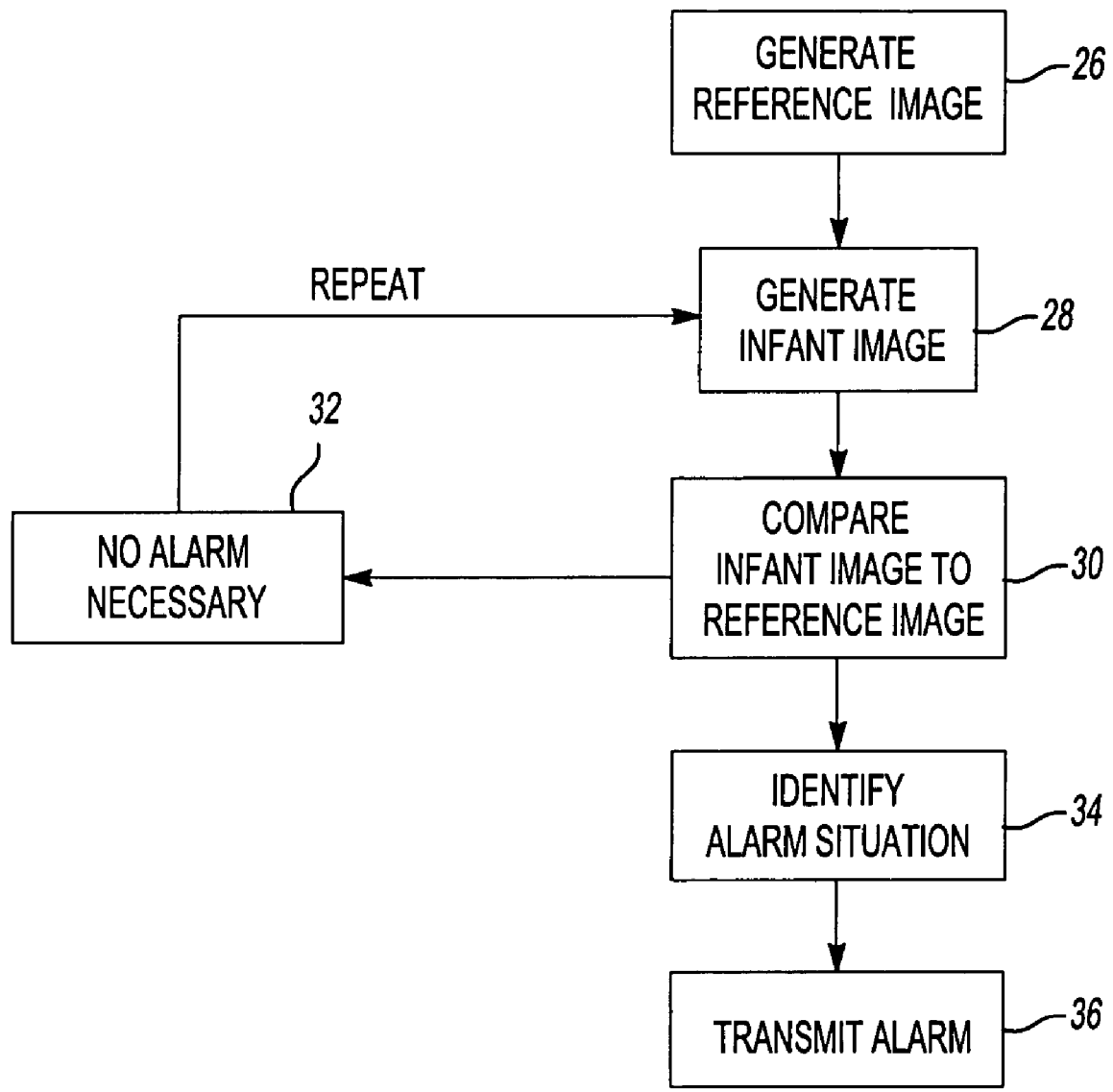
FIG. 2 shows a flow diagram of the logic pattern used by the inventive sudden infant death syndrome method.

As shown in FIG. 2, a second electronic image 28 of the infant is generated once the infant has been placed in the crib 12 for sleep. The camera 16 signals the processor 20 the location of a second plurality of pixels corresponding to the infant's 14 sleeping position.

The second plurality of pixels corresponding to the second image 28 is compared by the processor 20 against the reference image 26 by way of a computer algorithm as set forth in block 30 using statistical analysis to determine the correlation between the second image 28 and the reference image 26. For example, if the second image 28 includes the characteristics of the infant 14 identified in the reference image 26, the processor 20 will signal the camera 16 to continue to sequentially relay images of the sleeping infant 14 over a period of time to monitor the infant's sleeping pattern set forth in block 32. Alternatively, if the reference image 26 is made of the side of the infant 14, the second image 28 is compared against features such as, for example, the infant's 14 profile, ear, or shoulder.

When the processor 20 determines the infant 14 has moved to a high risk position, either face down or on the infant's 14 side, an alarm situation is identified 34, and a distress signal 30 is generated and transmitted 36 to the plurality of remote locations 24 notifying the infant's 14 caregiver. In the event that the processor 20 does not determine the infant has performed a high risk movement, the camera 16 continues to generate sequential images, from which the processor 20 compares against the reference image 26. Preferably, the camera 16 generates an image in just a fraction of a second where the camera can also detect symptoms such as rapid eye blinking, erratic breathing, jerking movements, and the like, each of which trigger a distress signal 36 to the infant's 14 caregiver.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, wherein reference numerals are merely for convenience and are not to be in any way limiting, the invention may be practiced otherwise than as specifically described.

The invention claimed is:

1. A method of detecting high risk movements of an infant relating to Sudden Infant Death Syndrome, comprising the steps of:
   providing a camera to generate a first electronic image of the infant by signaling a controller a location of a first plurality of pixels thereby generating a reference image representative of the front of the infant;
   generating a second electronic image of the infant by the camera and signaling said controller the location of a second plurality of pixels corresponding to the infant's sleeping position;
   comparing said second electronic image to said first electronic image for detecting a high-risk position of the infant; and
   determining if the infant has moved to said high risk position by comparing said first plurality of pixels to said second plurality of pixels;
   sounding an alarm if the infant has rolled completely over or onto the side of the infant corresponding to said high risk position prior to any disruption in the infant's breathing pattern.

2. The method as set forth in claim 1, further including the step of generating sequential electronic images through said first plurality of pixels and said second plurality of pixels, respectively, thereby monitoring the movement of the infant over a period of time.

3. The method as set forth in claim 1, wherein the step of sounding an alarm is further defined by transmitting a distress signal to a plurality of remote locations.

4. The method as set forth in claim 2, further including the step of transmitting non-visible light waves onto the infant thereby enhancing the sequential electronic images.

5. The method as set forth in claim 3, wherein said step of generating the sequential electronic images is further defined by receiving said non-visible light waves.

6. The method as set forth in claim 1, further including the step of distinguishing the infant from static pixels generated by an electronic image of static background.

7. The method as set forth in claim 1, wherein said step of providing a camera is further defined by providing a charge-coupled camera.

8. The method as set forth in claim 1, wherein said step of providing a camera is further defined by providing a high dynamic range camera.

9. The method as set forth in claim 1, wherein said step of providing a camera is further defined by providing an active pixel camera.

10. The method as set forth in claim 1, wherein said step of providing a camera is further defined by providing an complementary metal oxide semiconductor camera.

11. The method as set forth in claim 2, wherein said steps of generating the sequential electronic images is further defined by obtaining first and said second electronic images by detecting electromagnetic radiation.

* * * * *

UNITED STATES PATENT AND TRADEMARK OFFICE
CERTIFICATE OF CORRECTION

| | | |
|---|---|---|
| PATENT NO. | : 7,035,432 B2 | Page 1 of 1 |
| APPLICATION NO. | : 10/896724 | |
| DATED | : April 25, 2006 | |
| INVENTOR(S) | : Joseph Szuba | |

It is certified that error appears in the above-identified patent and that said Letters Patent is hereby corrected as shown below:

In Figure 1, please insert --20-- in reference to the "processor."

In column 4, line 58, please delete "an" and insert --a--.

Signed and Sealed this

Fourth Day of September, 2007

JON W. DUDAS
*Director of the United States Patent and Trademark Office*